United States Patent [19]

Ruszala et al.

[11] 4,374,270

[45] Feb. 15, 1983

[54] OXYDEHYDROGENATION PROCESS FOR PREPARING METHACRYLIC ACID AND ITS LOWER ALKYL ESTERS

[75] Inventors: Ferdinand A. Ruszala, Columbus; Thomas J. Weeks, Jr., Arlington, both of Ohio

[73] Assignee: Ashland Oil, Inc., Ashland, Ky.

[21] Appl. No.: 328,289

[22] Filed: Dec. 7, 1981

[51] Int. Cl.$^3$ .................... C07C 51/377; C07C 57/05; C07C 67/317; C07C 69/54
[52] U.S. Cl. ................................... 562/599; 252/470; 252/472; 260/405.5; 560/214
[58] Field of Search .................... 562/599; 260/405.5; 560/214; 252/470, 472

[56] References Cited

U.S. PATENT DOCUMENTS 3,845,156 10/1974 Farha .................................. 252/437
3,948,959 4/1976 Cavaterra et al. .................. 562/599

Primary Examiner—Vivian Garner
Attorney, Agent, or Firm—John F. Jones

[57] ABSTRACT

Isobutyric acid or a lower alkyl ester thereof is oxidatively dehydrogenated in the vapor phase producing the corresponding $\alpha,\beta$-olefinically unsaturated derivative by contact with a heterogeneous catalyst in the presence of molecular oxygen. The catalyst is composed of the calcined oxides of iron and at least two members selected from the group consisting of antimony, niobium, tantalum and tungsten.

6 Claims, No Drawings

OXYDEHYDROGENATION PROCESS FOR PREPARING METHACRYLIC ACID AND ITS LOWER ALKYL ESTERS

BACKGROUND OF THE INVENTION

1. Field of the Invention

This invention relates to the conversion of isobutyric acid or its equivalents and lower alkyl esters thereof correspondingly to methacrylic acid or its equivalents and lower alkyl esters thereof.

2. Description of the Prior Art

There exists considerable prior art relating to the oxydehydrogenation of the lower saturated aliphatic monocarboxylic acids to produce the corresponding $\alpha,\beta$-olefinically unsaturated acids. Early work in this area involved thermal, vapor phase oxydehydrogenation of the saturated aliphatic carboxylic acid in the presence of oxygen and iodine. This approach has not been particularly successful from a commerical standpoint. This is understandably so inasmuch as iodine is costly and exhibits extreme corrosivity properties and recovery of comparatively large amounts thereof is required in the process. The heterogeneous catalytic method for oxydehydrogenation according to the prior art appears to be the more attractive route to the commercial production of olefinically unsaturated monocarboxylic acids. The prior art heterogeneous oxydehydrogenation catalysts useful for this purpose include some heteropoly acids such as phosphomolybdic acid optionally with tungsten and/or vanadium. Another type of catalyst included in the prior art is iron phosphate. For instance, U.S. Pat. No. 3,948,959 discloses that an alkali or alkaline earth metal can be included in an iron/phosphate catalyst useful for the oxydehydrogenation of isobutyric acid to methacrylic acid.

SUMMARY OF THE INVENTION

In accordance with this invention, a catalytic process is provided for the oxidative dehydrogenation of a saturated aliphatic monocarboxylic acid or lower alkyl ester thereof, such as isobutyric acid or methyl isobutyrate, to the corresponding $\alpha,\beta$-olefinically unsaturated derivative thereof, such as methyacrylic acid or methyl methacrylate. The process of this invention comprises contacting a heterogeneous catalyst at a temperature in the range of from 300°-500° C. with a mixture of the saturated aliphatic monocarboxylic acid and molecular oxygen, said catalyst being a calcined mixture of the oxides of iron and at least two members of the group consisting of antimony, niobium, tantalum and tungsten. The catalyst useful in this invention can be further defined by the gram-atom empirical formula $FeM_aO_x$ wherein a is a number from 0.5 to 3 and M represents at least two members selected from the group consisting of antimony, niobium, tantalum and tungsten and x represents a number determined by the valence requirement of the other elements present.

DESCRIPTION OF THE PREFERRED EMBODIMENT

There are a number of techniques which can be used for the preparation of the catalyst useful in the process of this invention. Of these, the more facile methods involve preparing the integral catalyst composition prior to calcination. This can be readily and conveniently accomplished by the so-called slurry method in which metal salts, either soluble or not, are mixed in a liquid medium such as water, the water is removed and the resulting solid is calcined producing the desired catalyst. In general, any compounds containing the desired catalyst components may be used provided that they result, upon calcination in the oxides of the instant catalyst. Suitable calcination temperatures range from 400°-1000° C. Applicable periods of calcination range from 2-30 hours although longer periods can be used without adverse results.

The use of a support or carrier for the catalyst is within the scope of the invention. The support can be included in the slurry preparation mentioned above. Useful carriers include alumina, pumice, silicon carbide, zirconia, titania, silica, alumina-silica, etc. The support when used can constitute from 3 percent to 99 percent and preferably between 5 percent and 95 percent by weight of the finished catalyst.

The process of this invention can be carried out using catalyst in the proper form for a fluidized bed reactor, a stirred tank reactor or for a fixed or packed bed reactor or any combination of these types of reactors. Because of the convenience associated with the use of a fixed bed reactor in a small scale operation, such a reactor will be exemplified herein. In the preferred mode of operation the feed to the reactor comprises a pre-heated gaseous mixture of the saturated aliphatic monocarboxylic acids, molecular oxygen, steam and inert diluent gas. In the case where methacrylic acid is produced from isobutyric acid it may be desirable to include some acetone in the feed to the reactor. A preheat temperature in the range of about 300° to 350° C. is customarily used. The oxydehydrogenation reaction can be carried out in the range of from 300° to 500° C. More generally a temperature of from 375° to 475° C. provides for optimum processing.

The mole ratio of molecular oxygen to carboxylic acid is from 0.2 to 1.5 and more preferably from 0.3 to 0.75 in the case where the carboxylic acid is isobutyric acid, per se. Although steam is not necessary for the reaction, its presence is desirable in the feed because it is believed to act beneficially as a heat sink and in minimizing combustion of the carboxylic acid to undesirable products. The mole ratio of water to the carboxylic acid in the feed should be from about 2 to 20. The optimum ratio is from 6 to 12.

Another important parameter is the concentration of the organic reactant in the feed. The organic reactant carboxylic acid or ester should be present in the feed in from 0.1 to 20 mole percent. From the standpoint of achieving a reasonable throughput combined with an acceptable yield, the concentration of the reactant in the feed is from about 3-30 mole percent. Concentration of reactant in the feed is controlled to a large degree by the amount of inert gas present. The preferred inert gas or diluent is nitrogen although other inert gases such as carbon dioxide, helium, argon, and the like are suitable. Air is a very convenient source of oxygen plus inert diluent.

Another important parameter is contact time in the process of this invention. Contact or reaction time is defined for the purpose of this invention as the catalyst volume divided by the volume of gas feed per second at the reaction temperature. The catalyst volume is the bulk volume occupied by the catalyst in the reactor. The term catalyst in this sense not only includes the material identified by the empirical formula above but also includes the support material if present. Accordingly, reaction times can range from 0.05 to 3.0 seconds and more generally in the range of from 0.1 to 1.0 second. The reaction is preferably carried out at or near atmospheric pressure although the use of higher pressures up to about 10 atmospheres is contemplated.

The process of this invention is further illustrated in the following specific examples.

EXAMPLE I

This example illustrates the use of the slurry method for preparing the catalysts of this invention. A slurry of 20.20 g. Fe(NO$_3$)$_3$.9H$_2$O, 4.45 g. of Sb$_2$O$_5$, and 6.38 g. of WO$_3$ in 100 ml. of water was dried overnight at 120° C. The nitrates in the resulting solid were decomposed at 350° C. for 24 hours and the resulting solid was ground under acetone and calcined at 980° C. for two days. The use of this and similarly prepared catalysts in the oxydehydrogenation reaction is described in the following examples.

EXAMPLE II

This example illustrates the use of the catalysts described in Example I in the oxydehydrogenation of isobutyric acid to produce methacrylic acid. The procedure consisted of feeding a preheated mixture of isobutyric acid, air and acetone. 0.5 g. of catalyst was run in a reactor which was a stainless steel tube 2″ long with ½″ O.D. and ⅜″ I.D. The feed mixture composed of 1080 cc. of water, 336 cc. of isobutyric acid, and 55 cc. of acetone was fed at a rate of 5.7 cc. per hour. The oxygen (as air) was fed at the same time at the rate of 20 standard cc. per minute. The reaction temperatures used and results obtained with various catalysts are given in the following table.

TABLE

| Catalyst | Reaction Temp., °C. | % Conversion of Isobutyric Acid | % Selectivity to Methacrylic Acid |
|---|---|---|---|
| FeSb$_{0.5}$W$_{0.5}$O$_x$ | 415 | 22.63 | 54.26 |
| FeNb$_{0.5}$Ta$_{0.5}$O$_x$ | 418 | 32.94 | 52.76 |
| FeSb$_{0.33}$Nb$_{0.33}$W$_{0.33}$O$_x$ | 416 | 21.26 | 58.41 |
| FeNb$_{0.33}$Ta$_{0.33}$W$_{0.33}$O$_x$ | 416 | 15.26 | 52.27 |

We claim:

1. A process for the catalytic conversion of isobutyric acid or a lower alkyl ester thereof to the corresponding $\alpha,\beta$-olefinically unsaturated derivative by oxydehydrogenation wherein a catalyst is contacted with a gaseous feed stream containing said acid or ester and molecular oxygen at a temperature between about 300° and 500° C. which comprises using as catalyst a material having the gramatom empirical formula FeM$_a$O$_x$ wherein a is a number from 0.5 to 3 and M is at least two members selected from the group consisting of antimony, niobium, tantalum and tungsten and x represents a number determined by the valence requirements of the other elements present.

2. The process of claim 1 wherein isobutyric acid is converted to methacrylic acid.

3. The process of claim 2 wherein the catalyst has the gram-atom empirical formula FeSb$_{0.5}$W$_{0.5}$O$_x$.

4. The process of claim 2 wherein the catalyst has the gram-atom empirical formula FeNb$_{0.5}$Ta$_{0.5}$O$_x$.

5. The process of claim 2 wherein the catalyst has the gram-atom empirical formula FeSb$_{0.33}$Nb$_{0.33}$W$_{0.33}$O$_x$.

6. The process of claim 2 wherein the catalyst has the gram-atom empirical formula FeNb$_{0.33}$Ta$_{0.33}$W$_{0.33}$O$_x$.

* * * * *